United States Patent
Friedrich et al.

(10) Patent No.: US 9,481,643 B2
(45) Date of Patent: Nov. 1, 2016

(54) FLUOROSURFACTANTS

(71) Applicant: MERCK PATENT GMBH, Darmstadt (DE)

(72) Inventors: Reiner Friedrich, Seeheim-Jugenheim (DE); Gerhard Jonschker, Heppenheim (DE); Fanny Schooren, Ober-Ramstadt (DE); Christian Depner, Gabsheim (DE); Steffen Schellenberger, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/416,003

(22) PCT Filed: Jul. 16, 2013

(86) PCT No.: PCT/EP2013/002112
§ 371 (c)(1),
(2) Date: Jan. 20, 2015

(87) PCT Pub. No.: WO2014/012661
PCT Pub. Date: Jan. 23, 2014

(65) Prior Publication Data
US 2015/0246875 A1 Sep. 3, 2015

(30) Foreign Application Priority Data

Jul. 18, 2012 (EP) .................................... 12005257

(51) Int. Cl.
| | |
|---|---|
| *C07C 19/08* | (2006.01) |
| *C07C 309/17* | (2006.01) |
| *C07C 43/12* | (2006.01) |
| *C07C 69/66* | (2006.01) |
| *C07C 211/02* | (2006.01) |

(Continued)

(52) U.S. Cl.
CPC ............. *C07C 309/17* (2013.01); *C07C 19/08* (2013.01); *C07C 43/12* (2013.01); *C07C 43/137* (2013.01); *C07C 69/657* (2013.01); *C07C 69/66* (2013.01); *C07C 211/02* (2013.01); *C07C 211/15* (2013.01); *C11D 1/004* (2013.01)

(58) Field of Classification Search
CPC ..................................................... C07C 19/08
See application file for complete search history.

(56) References Cited

U.S. PATENT DOCUMENTS

| | | | |
|---|---|---|---|
| 4,946,935 A | 8/1990 | Ohsaka et al. | |
| 4,968,599 A | 11/1990 | Pitt et al. | |

(Continued)

FOREIGN PATENT DOCUMENTS

| | | |
|---|---|---|
| EP | 0284331 A1 | 9/1988 |
| EP | 0285160 A2 | 10/1988 |

(Continued)

OTHER PUBLICATIONS

JP2004018394A, Jan. 2004, pp. 1-14; English translation.*

(Continued)

*Primary Examiner* — Fereydoun G Sajjadi
*Assistant Examiner* — Medhanit Bahta
(74) *Attorney, Agent, or Firm* — Millen White Zelano and Branigan, PC

(57) ABSTRACT

The present invention relates to novel compounds containing fluorinated end groups, to the use thereof as surface-active substances, and to compositions comprising these compounds.

21 Claims, 2 Drawing Sheets

Static surface tension γ of the sulfosuccinate according to Example 4

(51) Int. Cl.
  *C07C 211/15* (2006.01)
  *C11D 1/00* (2006.01)
  *C07C 43/13* (2006.01)
  *C07C 69/657* (2006.01)

(56) References Cited

U.S. PATENT DOCUMENTS

| | | | |
|---|---|---|---|
| 4,988,610 A | 1/1991 | Pitt et al. | |
| 6,706,923 B2 | 3/2004 | Haniff et al. | |
| 6,890,608 B2 | 5/2005 | Morishima et al. | |
| 7,692,035 B2 * | 4/2010 | Murphy | C07C 69/65 560/190 |
| 7,811,473 B2 | 10/2010 | Nagai et al. | |
| 7,989,566 B2 | 8/2011 | Coughlin et al. | |
| 7,999,049 B2 | 8/2011 | Coughlin et al. | |
| 8,008,358 B2 | 8/2011 | Kirsch et al. | |
| 8,263,800 B2 | 9/2012 | Murphy et al. | |
| 2003/0153780 A1 | 8/2003 | Haniff et al. | |
| 2003/0194378 A1 | 10/2003 | Rogueda et al. | |
| 2008/0093582 A1 | 4/2008 | Nagai et al. | |
| 2008/0149878 A1 | 6/2008 | Kirsch et al. | |
| 2009/0186969 A1 | 7/2009 | Coughlin et al. | |
| 2009/0186997 A1 | 7/2009 | Coughlin et al. | |
| 2009/0324834 A1 | 12/2009 | Hanson et al. | |
| 2010/0003737 A1 | 1/2010 | Murphy et al. | |
| 2011/0088594 A1 | 4/2011 | Claus et al. | |
| 2011/0118428 A1 | 5/2011 | Hierse et al. | |
| 2011/0257423 A1 | 10/2011 | Coughlin et al. | |
| 2012/0111233 A1 * | 5/2012 | Hierse | B01F 17/0035 106/499 |
| 2013/0269568 A1 | 10/2013 | Claus et al. | |

FOREIGN PATENT DOCUMENTS

| | | |
|---|---|---|
| EP | 1762566 A1 | 3/2007 |
| JP | 09111286 A | 4/1997 |
| JP | 2001133984 A | 5/2001 |
| JP | 2004018394 A * | 1/2004 |
| JP | 2010195937 A | 9/2010 |
| SU | 618367 A1 | 8/1978 |
| WO | 0203958 A1 | 1/2002 |
| WO | 03010128 A2 | 2/2003 |
| WO | 2006072401 A1 | 7/2006 |
| WO | 2006116222 A2 | 11/2006 |
| WO | 2009094344 A1 | 7/2009 |
| WO | 2009149807 A1 | 12/2009 |
| WO | 2010002623 A2 | 1/2010 |
| WO | 2010003567 A2 | 1/2010 |
| WO | 2010149262 A1 | 12/2010 |
| WO | 2011082770 A2 | 7/2011 |
| WO | 2012084118 A1 | 6/2012 |

OTHER PUBLICATIONS

International Search Report for PCT/EP2013/002112 dated Oct. 21, 2013.
Pitt, A. R. et al., "The relationship between surfactant structure and limiting values of surface tension, in aqueous gelatin solution, with particular regard to multilayer coating," Colloids and Surfaces A: Physiochemical and Engineering Aspeacts, 1996, vol. 114, pp. 321-335.
Liu, Z. et al., "Phase Behaviors of aerosol-OT Analogue Fluorinated Surfactants in 1,1,1,2-Tetrafluoroethane and Supercritical CO2," Ind. Eng. Chem. Res., 2007, vol. 46, pp. 22-28.
Okura, M. et al., "Fluorine-containing organic peroxides, radical polymerization initiators, and manufacture of fluoropolymers with good heat stability and suppressed whitening, discoloration, and expansion," Sep. 9, 2010, XP002714399.
Ivanova, T. L. et al., "Hydroxyethylated alpha alpha dihydroperfluoroalcohols for preparation of nonfreezing polyacrylates," Aug. 5, 1978, XP002714400.
Nagai, T. et al., "Perfluoropolyether containing amphiphilic compounds and their uses," Jan. 22, 2004, XP002714401.
English Abstract of JP-2001 133984, Publication Date: May 18, 2001.
English Abstract of WO2011082770, Publication Date: Jul. 14, 2011.
English Abstract of JP2010-195937, Publication Date: Sep. 9, 2010.
English Abstract of JP-2004-018394, Publication Date: Jan. 22, 2004.
English Abstract of JP09111286, Publication Date: Apr. 28, 1997.

* cited by examiner

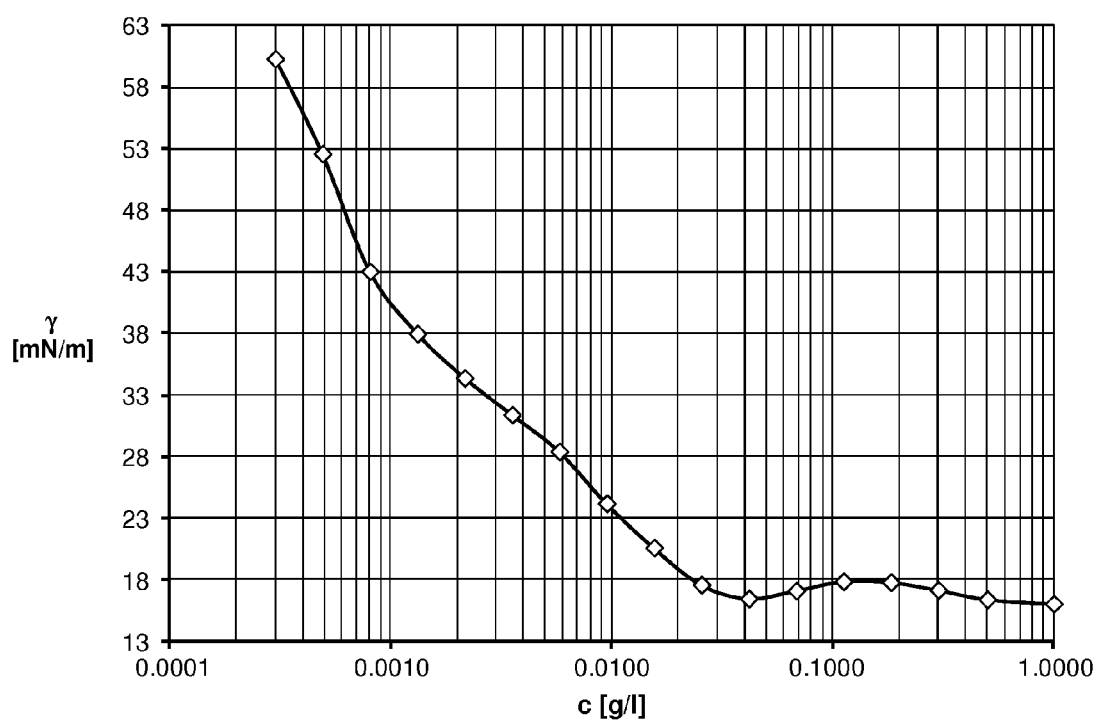
FIG 1: Static surface tension γ of the sulfosuccinate according to Example 4

FIG 2: Dynamic surface tensions γ of the sulfosuccinate according to Example 4
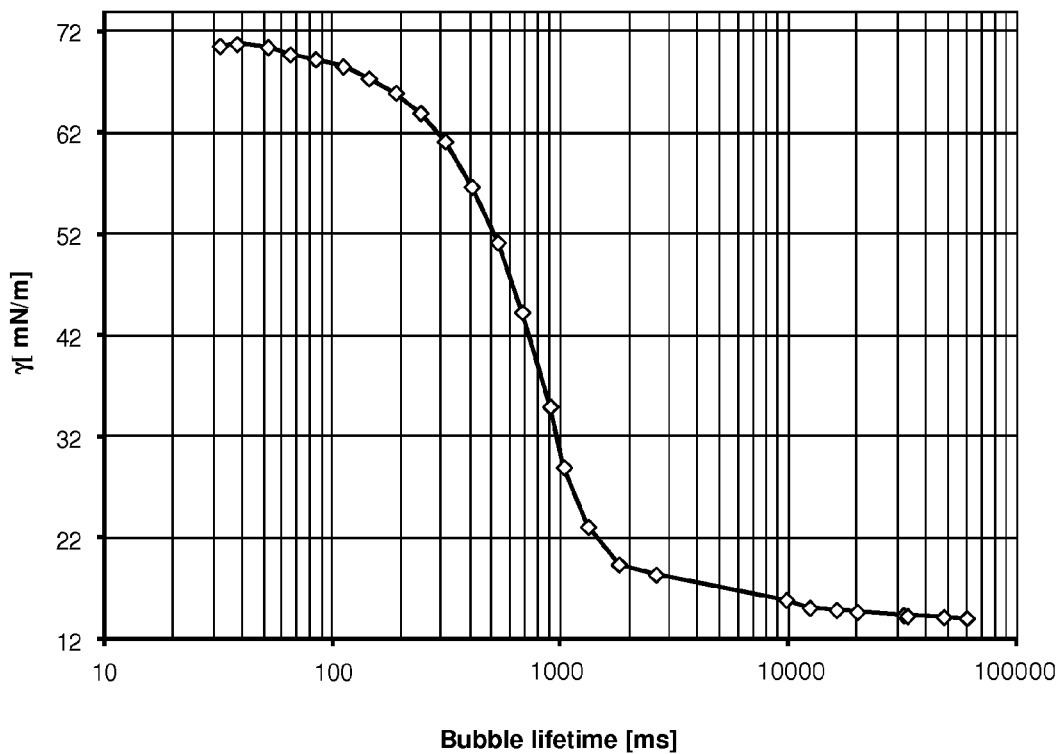

FLUOROSURFACTANTS

The present invention relates to novel compounds containing fluorinated end groups, to the use thereof as surface-active substances, and to compositions comprising these compounds.

Fluorosurfactants, whose static surface tension is very low (16-18 mN/m), can be employed in a very wide variety of applications and contribute, for example, to improved wetting of surfaces. Thus, for example, they are used as interface promoter or emulsifier or viscosity reducer in paints, lacquers or adhesives.

WO 03/010128 describes perfluoroalkyl-substituted amines, acids, amino acids and thioether acids which contain a C3-20-perfluoroalkyl group. JP-A-2001/133984 discloses surface-active compounds containing perfluoroalkoxy chains which are suitable for use in antireflection coatings. JP-A-09/111286 discloses the use of perfluoropolyether surfactants in emulsions. WO 2006/072401 and WO 2010/003567 describe surface-active compounds containing trifluoromethoxy groups. Compounds containing specific fluoroalkyl groups are described in U.S. Pat. No. 7,635,789, US 2008/0093582, JP 2004-18394 and WO 2010/002623. In addition, the compound $CF_3$—$CF_2$—$CF_2$—O—$CH_2$—$CH_2$—OH is known (CAS 1313023-37-8), and theoretical investigations on mixtures of $CO_2$ and perfluoroalkyl surfactants in aqueous solutions are described in J. of Supercritical Fluids 55 (2010) 802-816.

Specific applications of sulfosuccinates and/or sulfotricarballylates containing various fluorinated side chains are described in U.S. Pat. Nos. 4,968,599 and 4,988,610 and 6,890,608 and in A. R. Pitt et al., Colloids and Surfaces A: Physicochemical and Engineering Aspects, 1996, 114, 321-335; A. R. Pitt, Progr. Colloid Polym. Sci, 1997, 103, 307-317 and Z.-T. Liu et al., Ind. Eng. Chem. Res. 2007, 46, 22-28. Further fluorosurfactants, in particular succinates and tricarballylates containing fluorinated alkyl groups, are described in WO 2009/149807, WO 2010/003567, WO 2010/149262, WO 2011/082770 and WO 2012/084118.

There continues to be a demand for alternative surface-active substances, preferably having a property profile comparable to classical fluorosurfactants, which preferably on degradation do not degrade to form long-chain persistent compounds or are preferably equally effective as conventional fluorosurfactants in lower dosage.

Novel compounds which are suitable as surface-active substances and preferably do not have one or more of the above-mentioned disadvantages have now been found.

The present invention relates firstly to compounds of the formula (I)

$$(R_f\text{-}A_a\text{-}C_c)_n\text{-}(\text{spacer})_m\text{-}X_o \quad (I)$$

where
Rf=$CF_3$—$CF_2$—$CF_2$—O—$CF(CF_3)$—$CH_2$—, $CF_3$—$CF_2$—$CF_2$— or $CF_3$—$CF_2$—$CF_2$—O—$CF(CF_3)$—CO—,
A=—O—$CH_2$—CHR'—,
R'=H or alkyl,
C=alkylene, O, —OCO— or —NR"—, where R"=H, alkyl, or —($CH_2CHR'''$)$_{m'}$—R"", where m'=an integer from the range from 1 to 100 and R''' and R"", independently of one another, =H or alkyl, where one or more non-adjacent C atoms may be replaced by O or N, preferably O,
spacer=a saturated or unsaturated, branched or unbranched hydrocarbon unit, optionally containing heteroatoms,
X is a hydrophilic group,
a=0 or 1,
n=1, 2, 3, 4, 5 or 6,
c=0 or 1,
m=0 or 1,
o=1, 2, 3 or 4, and o=0 if R"=—($CH_2CHR'''$)$_{m'}$—R"", where R''' and/or R""=alkyl, where one or more non-adjacent C atoms have been replaced by O or N,
where n≥2 if Rf=$CF_3$—$CF_2$—$CF_2$—O—$CF(CF_3)$—CO— and the compounds $CF_3$—$CF_2$—$CF_2$—O—$CH_2$—$CH_2$—OH,
Rf'-O—$CH_2CH(OSO_3Na)$—$CH_2$—O—$CH_2$—CH—($C_2H_5$)—$C_4H_9$,
Rf'-O—$CH_2CH(OSO_3H)$—$(CH_2)_5$—$CH_3$,
Rf'-O—CO—$CH_2$—$CH(OSO_3Na)$—CO—O—Rf',
Rf"-$CH_2$—$CH(SO_3Na)$—Rf",
Rf"-$CH_2$—$CH(CH_2SO_3Na)$—Rf" and
Rf"-CH—$(CH_3)CH(SO_3Na)$—Rf",
where Rf'=$CF_3CF_2CF_2$—O—$CF(CF_3)$—$CH_2$— and Rf"=$CF_3CF_2CF_2$—O—$CF(CF_3)$—CO—$NHCH_2CH_2$—O—CO—, are excluded.

The hydrocarbon units of the spacer of the compounds of the formula (I) can be aliphatic or aromatic units, optionally provided with heteroatoms. The group $(R_f\text{-}A_a\text{-}C_c)_n$ in the surface-active compounds is preferably bonded to a saturated, branched or unbranched hydrocarbon unit, preferably to a saturated, branched or unbranched alkylene group, where one or more non-adjacent C atoms may be replaced by O or N, preferably O. In a variant of the invention, the preferred hydrocarbon unit containing heteroatoms used is a polyethylene or polypropylene glycol unit.

In a variant of the invention, the group $(R_f\text{-}A_a\text{-}C_c)_n$ occurs multiple times, preferably twice or three times, in the surface-active compound. In another variant of the invention, the group $(R_f\text{-}A_a\text{-}C_c)_n$ only occurs once in the surface-active compound.

R''' is preferably equal to H or alkyl, in particular C1-C4 alkyl. R"" is preferably equal to alkyl, where one or more non-adjacent C atoms may be replaced by O.

Preference is given to compounds of the formula (I) in which:
Rf=$CF_3$—$CF_2$—$CF_2$—O—$CF(CF_3)$—$CH_2$—,
A=—O—$CH_2$—CHR'—,
R'=H or C1-C4 alkyl, preferably H, $CH_3$ or $C_2H_5$, in particular H,
C=C1-C4, preferably C1-C2, alkylene, O or —OCO—
spacer=a linear or branched hydrocarbon unit, optionally provided with heteroatoms,
X is an anionic, cationic, non-ionic or amphoteric group,
a=0 or 1, preferably 1,
n=1, 2, or 3,
c=1,
m=0 or 1, preferably 1,
o=1 or 2.

Further preferred compounds of the formula (I) are those in which:
Rf=$CF_3$—$CF_2$—$CF_2$—O—$CF(CF_3)$—CO—,
C=—NR"—, where R"=H, alkyl, or —($CH_2CHR'''$)$_{m'}$—R"", where m'=an integer from the range from 1 to 100 and R'''=H or C1-C4-alkyl and R""=alkyl, where one or more non-adjacent C atoms may be replaced by O,
spacer=linear or branched alkylene,
X is an anionic, cationic, non-ionic or amphoteric group,
a=0,
n=2 or 3, preferably 2,
c=1,
m=1,
o=1 or 2 and o=0 if R"=—($CH_2CHR'''$)$_{m'}$—R"".

R" is preferably equal to H or C1-C4 alkyl, preferably C1-C2 alkyl.

In a variant of the invention, R" is preferably equal to —(CH$_2$CHR''')$_{m'}$—R'''', preferably where m'=1 to 30, in particular 1-15, and R'''=H or CH$_3$ and R''''=alkyl, where one or more non-adjacent C atoms have been replaced by O.

In the compounds of the formula (I), Rf may also be equal to CF$_3$—CF$_2$—CF$_2$—. Preferably here, a=1 and/or c=1 and/or m=1. Then preferably, C=O.

The compounds of the formula (I) preferably contain two or three Rf group.

Particular preference is given to compounds of the formula (II):

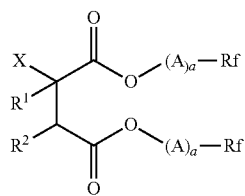

(II)

where
Rf=CF$_3$—CF$_2$—CF$_2$—O—CF(CF$_3$)—CH$_2$—,
A=—O—CH$_2$—CHR'—,
R'=H, CH$_3$, C$_2$H$_5$
X is an anionic, cationic, non-ionic or amphoteric group,
R$^1$=hydrogen or —CH$_2$—COO-(A)$_a$-Rf,
R$^2$=hydrogen, —CH$_2$—COO-(A)$_a$-Rf or X
a=0 or 1, preferably 1.

A further preferred variant of the invention are compounds of the formula (III):

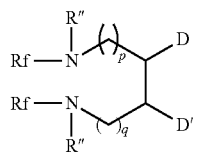

(III)

where
Rf=CF$_3$—CF$_2$—CF$_2$—O—CF(CF$_3$)—CO— or =Rf',
where Rf'=CF$_3$—CF$_2$—CF$_2$—O—CF(CF$_3$)—CH$_2$—O—CH$_2$—CHR'—,
p=1-10,
q=1-10 and
R' and R" have the meanings described for formula (I), in particular the preferred meanings described.
D and/or D' are equal to H or X, where at least one group must be equal to X if R"=H or alkyl. X is preferably an anionic, cationic, non-ionic or amphoteric group. p and q are preferably, independently of one another, 1-4, in particular 1-2. p and q are preferably identical. Rf in formula (III) is preferably equal to CF$_3$—CF$_2$—CF$_2$—O—CF(CF$_3$)—CO—.

In a variant of the invention, R'''' in the formula (III) is equal to the non-ionic group —Y—(CH$_2$—CH$_2$—O)$_v$—R$^4$, where Y=O, R$^4$=H or alkyl, preferably H or CH$_3$, and v=1-100, preferably 1-20, in particular 1-15, described below as an example of a hydrophilic group X.

Preference is also given to compounds of the formula (IV)

R$_f$-A$_a$-C-(spacer)$_m$-X (IV)

where
Rf=CF$_3$—CF$_2$—CF$_2$—O—CF(CF$_3$)—CH$_2$—,
A=—O—CH$_2$—CHR'—,
R'=H or alkyl, preferably CH$_3$ or C$_2$H$_5$,
C=alkylene, preferably C1 alkyl, or O,
X is an anionic, cationic, non-ionic or amphoteric group, spacer has the meanings described for formula (I), in particular the preferred meanings,
a=0 or 1, preferably 1, and
m=0 or 1.

In the formulae (II) to (IV), in particular (II) and (III), Rf may also be equal to CF$_3$—CF$_2$—CF$_2$—.

In the compounds according to the invention, X is a hydrophilic group, preferably an anionic, cationic, nonionic or amphoteric group.

A preferred anionic group X can be selected from —COO$^-$, —SO$_3^-$, —OSO$_3^-$, —PO$_3^{2-}$, —OPO$_3^{2-}$, —(OCH$_2$CH$_2$)$_s$—O—(CH$_2$)$_t$—COO$^-$, —(OCH$_2$CH$_2$)$_s$—O—(CH$_2$)$_t$—SO$_3^-$, —(OCH$_2$CH$_2$)$_s$—O—(CH$_2$)$_t$—OSO$_3^-$, —(OCH$_2$CH$_2$)$_s$—O—(CH$_2$)$_t$—PO$_3^{2-}$, —(OCH$_2$CH$_2$)$_s$—O—(CH$_2$)$_t$—OPO$_3^{2-}$ or from the formulae A to C,

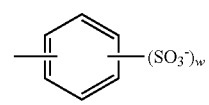

A

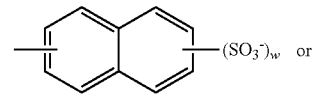

B or

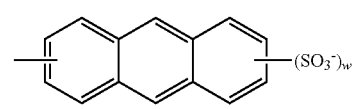

C where s stands for an integer from the range from 1 to 1000, t stands for an integer selected from 1, 2, 3 or 4 and w stands for an integer selected from 1, 2 or 3.

The preferred anionic groups here include, in particular, —COO$^-$, —SO$_3^-$, —OSO$_3^-$, —PO$_3^{2-}$, —OPO$_3^{2-}$, the sub-formula A, and —(OCH$_2$CH$_2$)$_s$—O—(CH$_2$)$_t$—COO$^-$, —(OCH$_2$CH$_2$)$_s$—O—(CH$_2$)$_t$—SO$_3^-$ and —(OCH$_2$CH$_2$)$_s$—O—(CH$_2$)$_t$—OSO$_3^-$, where each individual one of these groups may be preferred per se.

The very particularly preferred anionic groups here include —SO$_3^-$, —OSO$_3^-$, —PO$_3^{2-}$ or OPO$_3^{2-}$. Particular preference is given to a sulfonate group —SO$_3^-$.

The preferred counterion for anionic groups X is a monovalent cation, in particular H$^+$, an alkali metal cation or NR$_4^+$, where R is H or C1-C6-alkyl and all R may be identical or different. Particular preference is given to Na$^+$, K$^+$, Li$^+$ and NH$_4^+$, particularly preferably Na$^{30}$ A preferred cationic group X can be selected from —NR$^1$R$^2$R$^{3+}$Z$^-$, —PR$^1$R$^2$R$^{3+}$Z$^-$,

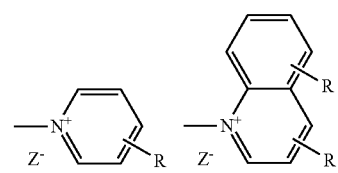

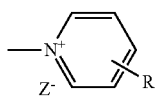

where R stands for H or $C_{1-4}$-alkyl in any desired position, $Z^-$ stands for $Cl^-$, $Br^-$, $I^-$, $CH_3SO_3^-$, $CF_3SO_3^-$, $CH_3PhSO_3^-$, $PhSO_3^-$, $R^1$, $R^2$ and $R^3$ each stand, independently of one another, for H, $C_{1-30}$-alkyl, Ar or —$CH_2$Ar and Ar stands for an unsubstituted or mono- or polysubstituted aromatic ring or condensed ring systems having 6 to 18 C atoms in which, in addition, one or two CH groups may be replaced by N.

The preferred cationic groups here include, in particular, —$NR^1R^2R^{3+}Z$ and

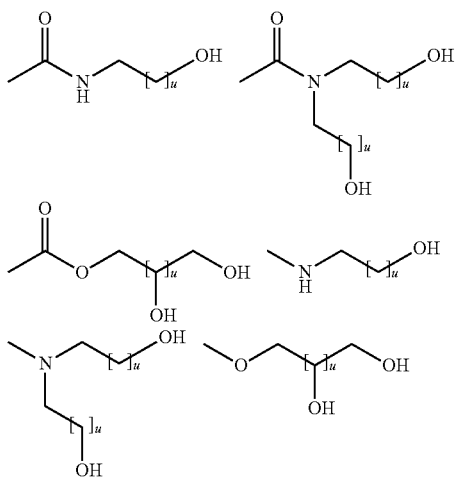

where each individual one of these groups per se may be preferred.

A preferred nonionic group can be selected from linear or branched alkyl, where one or more non-adjacent C atoms have been replaced by O, S, and/or N, —OH, —SH, —O-(glycoside)$_{o'}$, —S-(glycoside)$_{o'}$, —$OCH_2$—CHOH—$CH_2$—OH, —$OCH_2Ar(—NCO)_{p'}$, —$OAr(—NCO)_{p'}$, amine oxide, u stands for an integer from the range from 1 to 6, preferably 1 to 4,
o' stands for an integer from the range from 1 to 10,
p' stands for 1 or 2,
Ar stands for an unsubstituted, mono- or polysubstituted aromatic ring or condensed ring systems having 6 to 18 C atoms in which, in addition, one or two CH groups may be replaced by C=O and,
glycoside stands for an etherified carbohydrate, preferably for a mono-, di-, tri- or oligoglucoside.

The preferred nonionic groups here include, in particular, linear or branched alkyl, where one or more non-adjacent C atoms have been replaced by O, S and/or N, —OH and —O-(glycoside)$_{o'}$.

If X=alkyl, where one or more non-adjacent C atoms have been replaced by O, S and/or N, it is then preferably equal to $R^4$-(B-A)$_{m''}$-, where $R^4$=H or $C_{1-4}$-alkyl, in particular H or $CH_3$, A=linear or branched alkylene, preferably having 1 to 10 carbon atoms, in particular having 1 to 4 carbon atoms, B=O or S, preferably O, and m''=an integer preferably from the range from 1 to 100, particularly preferably 1 to 30.

The nonionic group X is particularly preferably the group $R^4$—(O—$CH_2CHR^5$)$_{m''}$—, where m''=an integer from the range from 1 to 100, preferably 1 to 30, in particular 1-15, and $R^4$ and $R^5$=H or $C_{1-4}$-alkyl, in particular H or $CH_3$. $R^4$-(B-A)$_{m''}$- is particularly preferably a polyethylene or polypropylene glycol unit.

The nonionic group X is particularly preferably the group —CH(OH)—$CH_2$—NH— Sach, where Sach=various sugars, and the group —Y—($CH_2$—$CH_2$—O)$_v$—$R^4$, where Y=S, O or NH, preferably O, $R^4$=H or alkyl, preferably H or $CH_3$, and v=1-100, preferably 1-20, in particular 1-15.

A preferred amphoteric group can be selected from the functional groups of the acetyldiamines, the N-alkylamino acids, the N-alkylaminosulfonic acids, the betaines, the sulfobetaines, or corresponding derivatives, in particular selected from, where M stands for H or an alkali-metal ion, preferably $Li^+$, $Na^+$ or $K^+$:

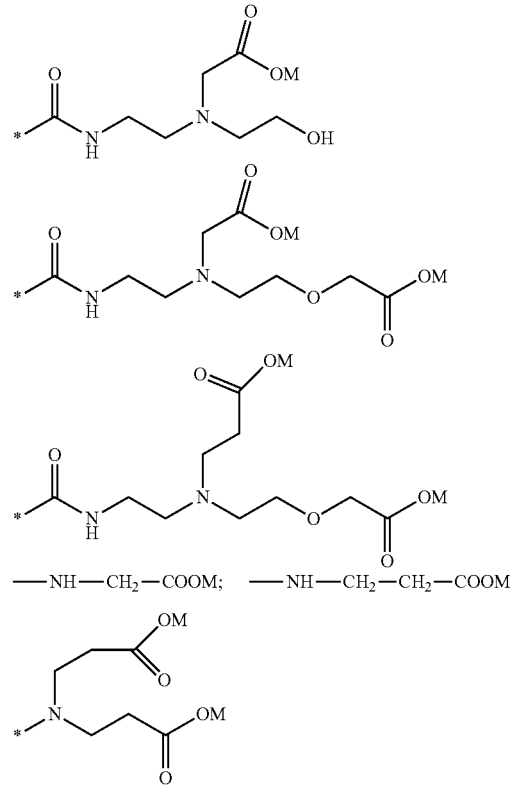

—[(C(=O)—NH—($CH_2$)$_{1-8}$]$_{(0\ or\ 1)}$—$N^+R^1R^2$—$CH_2COO^-$, where $R^1$ and $R^2$ each stand, independently of one another, for a C1-8-alkyl radical, preferably methyl or ethyl —C(=O)—NH—($CH_2$)$_{1-3}$—$N^+R^1R^2$—$CH_2$—CH(OH)—$CH_2$-(O)$_{(0\ or\ 1)}$—(S or P)$O_3^-$, where $R^1$ and $R^2$ each stand, independently of one another, for a C1-8-alkyl radical, preferably methyl or ethyl Particularly preferred compounds according to the invention are those which contain one of the preferred anionic groups, the preferred nonionic groups or the preferred zwitterionic groups as hydrophilic group X. Particular preference is given to compounds which contain the groups —$SO_3^-$, —$OSO_3^-$, —$PO_3^{2-}$ or $OPO_3^{2-}$, polyethylene glycol or polypropylene glycol, —CH(OH)—CH$_2$—NH-Sach, —Y—(CH$_2$—CH$_2$—O)$_v$—R$^4$, betaines, or sulfobetaines, in particular —SO$_3^-$. Preferred counterions here are Na$^+$, K$^+$ and NH$_4^+$, in particular Na$^+$. Particular preference is given to: —SO$_3^-$, polyethylene glycol or polypropylene glycol, sulfobetaines, the group —CH(OH)—CH$_2$—NH-Sach and the group —Y—(CH$_2$—CH$_2$—O)$_v$—R$^4$. Sach here=various sugars and Y=S, O or NH, preferably O, R$^4$=H or alkyl, preferably H or CH$_3$, and v=1-100, preferably 1-20, in particular 1-15. Particularly advantageous are compounds where X=-SO$_3^-$.

Particularly advantageous are compounds of the formula (I) in which one or more of the variables have the preferred meanings. Particularly advantageous are compounds of the formula (I) in which all said variables have the preferred meanings.

Particular preference is given to compounds of the formulae (II), (Ill) and (IV) in which one or more of the variables have the preferred meanings. Particular preference is given to the variants of the formulae (II) to (IV) in which all variables have the preferred meanings, especially the particularly preferred meanings. Particularly advantageous are compounds of the formula (II) in which all said variables have the preferred meanings.

Especial preference is given to compounds of the formulae (II-a) (II-b), (II-c) and (II-d) in which the variables have the meanings indicated for the formula (II), in particular the preferred meanings.

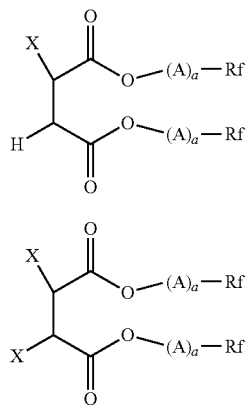

(II-a)

(II-b)

(II-c)

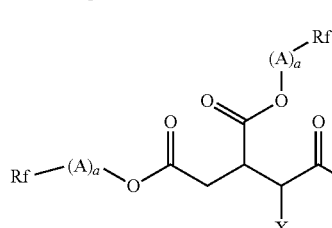

(II-d)

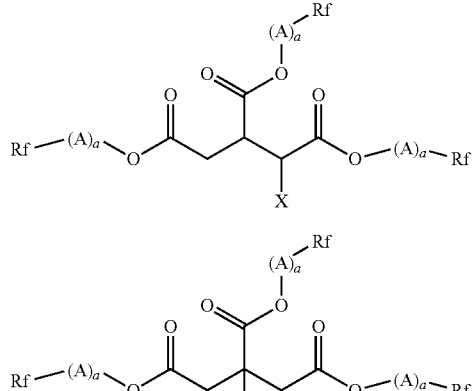

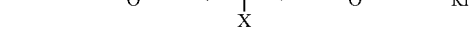

Examples of particularly advantageous compounds are the succinates of the formulae (II-a/1), (II-a/2), (II-a/3) and (II-a/4) and the corresponding tricarballylates, where R' has the meaning described above, in particular the preferred meanings:

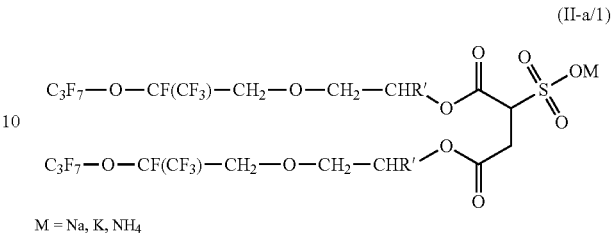

(II-a/1)

M = Na, K, NH$_4$

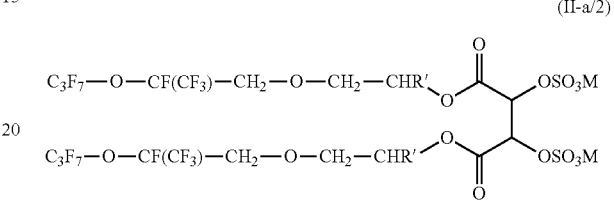

(II-a/2)

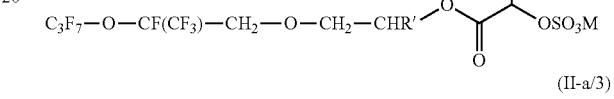

(II-a/3)

Sach = various sugars

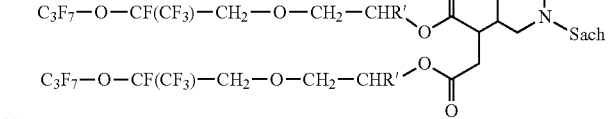

(II-a/4)

Y = S, O, NH;
v = 1-15

Preference is also given to compounds of the formulae (III-1) to (III-9), in particular of the formulae (III-6) to (III-9), where p, q, R' and R'' have the meanings described in accordance with formula (III), in particular the preferred meanings:

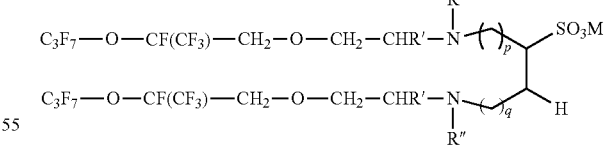

(III-1)

M = Na, K, NH4

(III-2)

M = Na, K, NH4

(III-3)
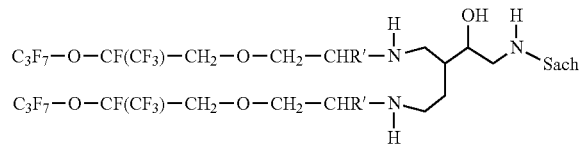
Sach = sugar
(III-4)
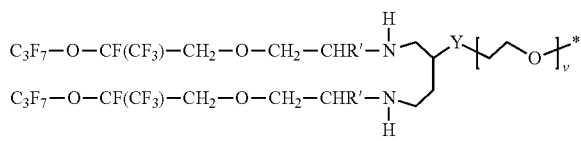
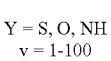
Y = S, O, NH
v = 1-100
(III-5)
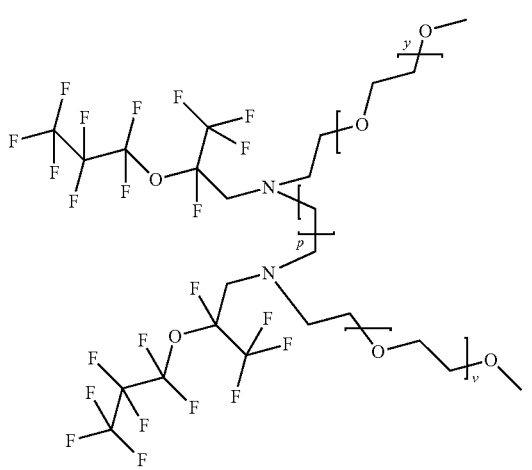
v = 1-100
(III-6)
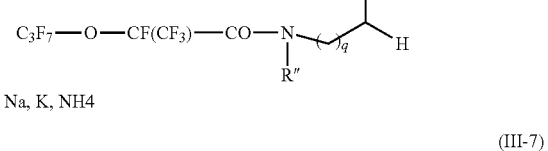
M = Na, K, NH4
(III-7)
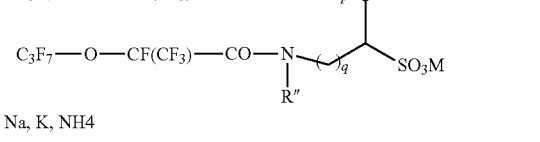
M = Na, K, NH4
(III-8)
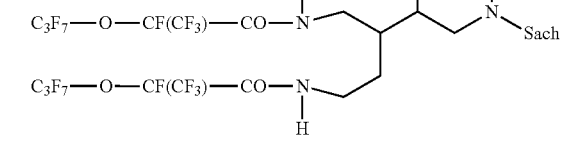
Sach = sugar
(III-9)
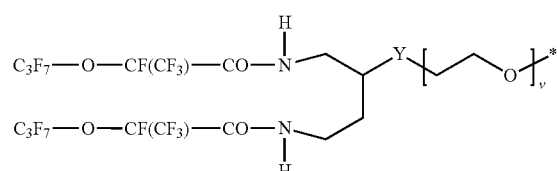
Y = S, O, NH
v = 1-100
Preferred examples of the formula (IV) are compounds of the formulae (IV-1) to (IV-8), where R' has the meaning described in accordance with formula (IV), in particular the preferred meanings:
(IV-1)
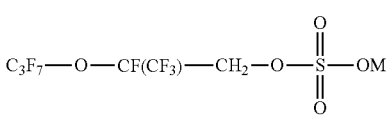
M = Na, K, NH4
(IV-2)
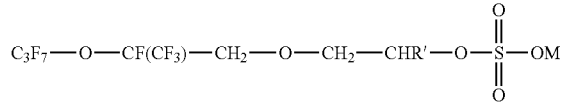
(IV-3)
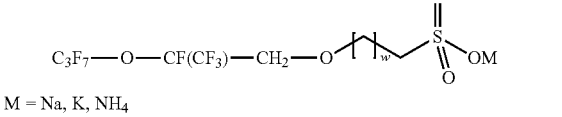
M = Na, K, NH4
w = 0-10, preferably 1-3
(IV-4)
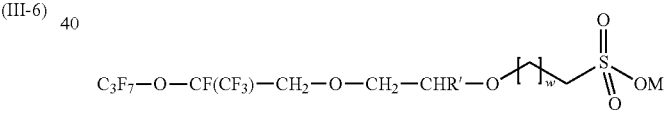
(IV-5)
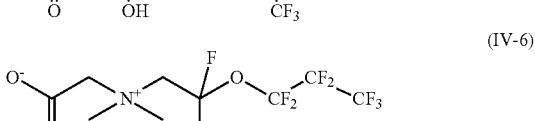
(IV-6)
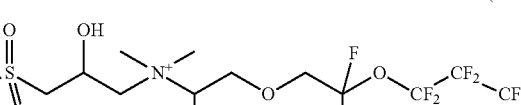
(IV-7)
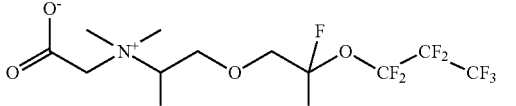
(IV-8)

Particularly advantageous are the preferred compounds of the formulae (II-a/1) and (II-a/2). The preferred counterion here is Na+

The compounds of the formula (II) according to the invention can preferably be prepared by esterification of maleic acid and aconitic acid or anhydrides or acid chlorides thereof using one or more alcohols of the formula (V), where Rf, A and a have the meanings or preferred meanings described for formula (II)

Rf-(A)$_a$-OH    (V)

and subsequent addition onto the double bond in order to introduce the group X.

The invention thus furthermore relates to the corresponding maleic acid and aconitic acid esters of the formulae (VI) and (VII):

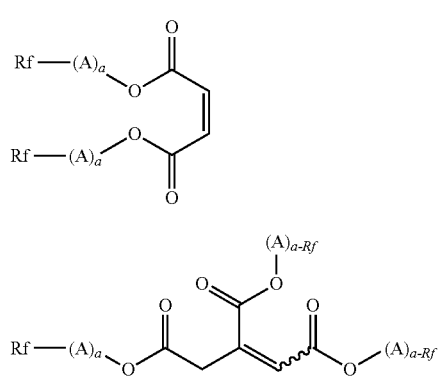

The variables in the formulae (VI) and (VII) have the meanings described for the formula (II), in particular also the preferred meanings. The formula (VII) shows the presence of Z/E double-bond isomers.

The compounds according to the invention can also preferably be prepared by esterification of hydroxysuccinic acid and citric acid using one or more alcohols of the formula (V) and subsequent functionalisation of the hydroxyl groups in order to introduce the group X.

The alcohols used are commercially available and/or their preparation starting from commercially available starting materials is familiar to the person skilled in the art or they can be prepared analogously to known synthetic processes, for example by reduction of methyl perfluoro(2-methyl-3-oxahexanoate (for example using LiAlH$_4$) and optional chain extension using ethylene carbonate under conditions known to the person skilled in the art.

The synthesis of succinates and tricarballylates according to the invention is preferably carried out in a two-step synthesis via the corresponding maleates or hydroxysuccinates or the corresponding aconitic or citric acid esters. The following schemes show this by way of example:

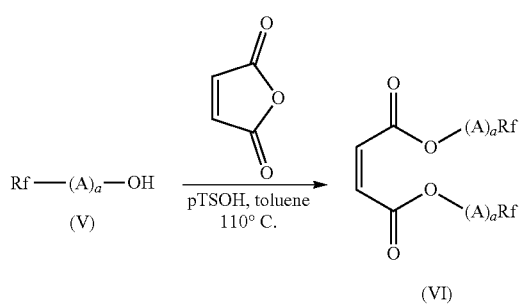

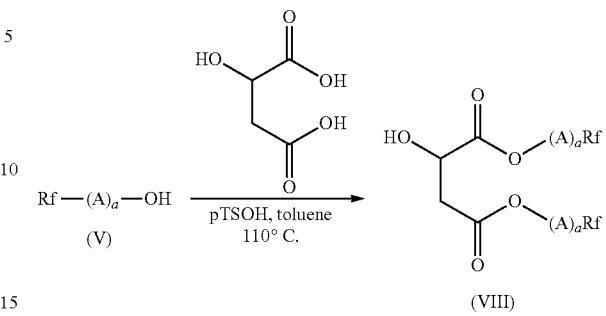

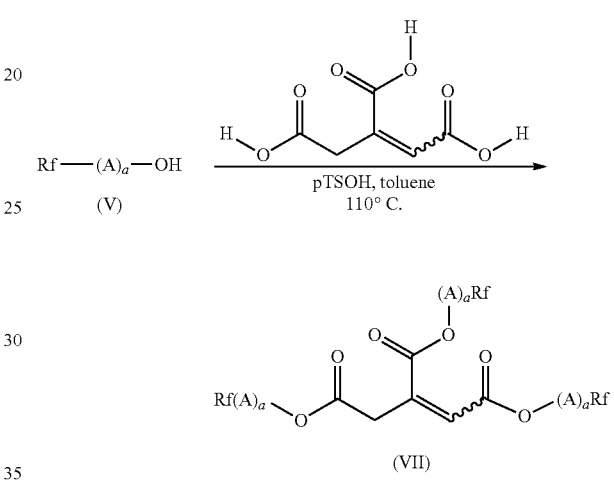

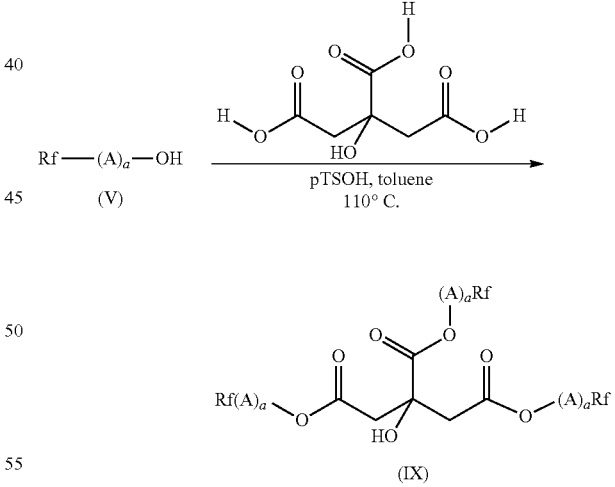

In a second step, the group X is then introduced by addition onto the double bond or derivatisation of the OH group by methods familiar to the person skilled in the art.

The following scheme shows by way of example the synthesis of the sulfotricarballylates by the addition of sodium hydrogensulfite, which can be carried out under conditions known to the person skilled in the art:

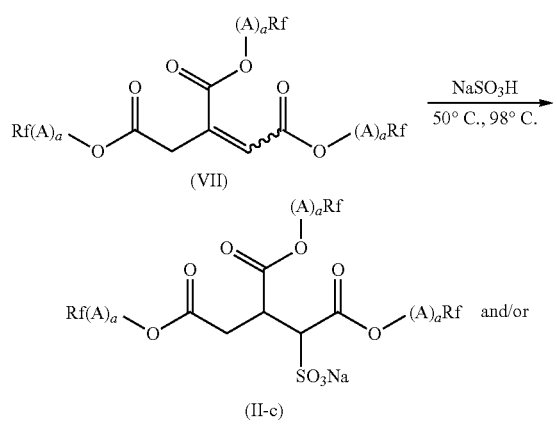
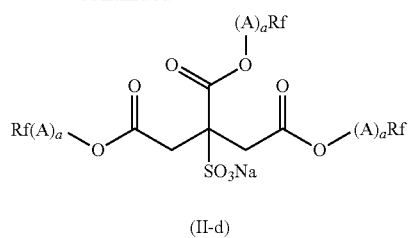
Further possibilities for the synthesis of non-ionic surfactants from citric/aconitic acid are shown by way of example in the following schemes, where preferably n=1-30.
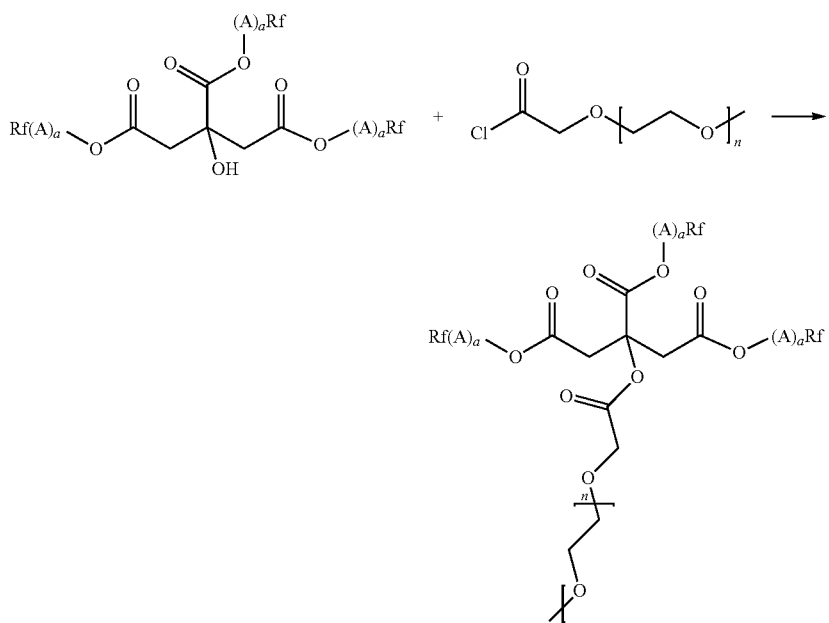
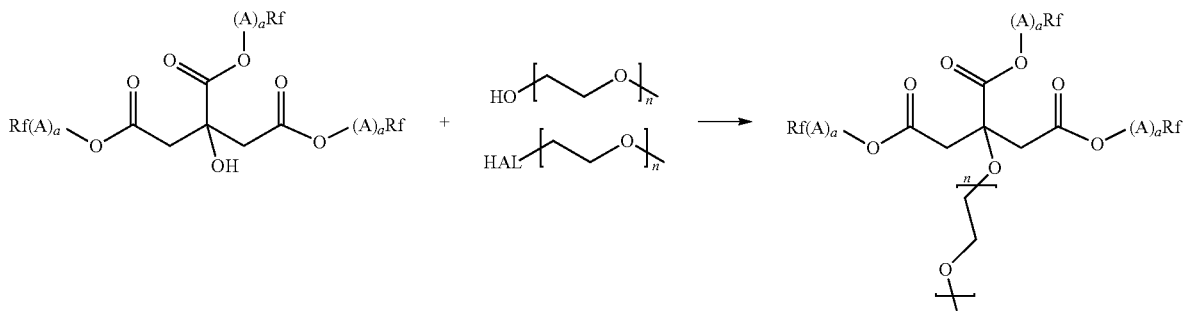
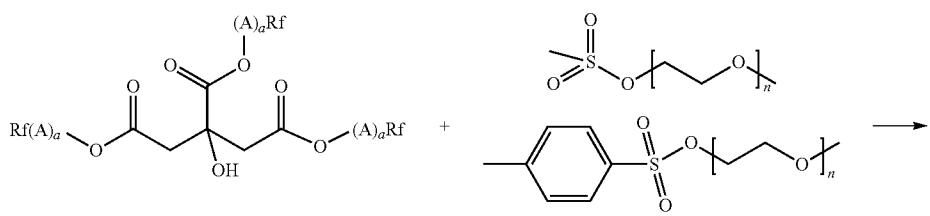

-continued

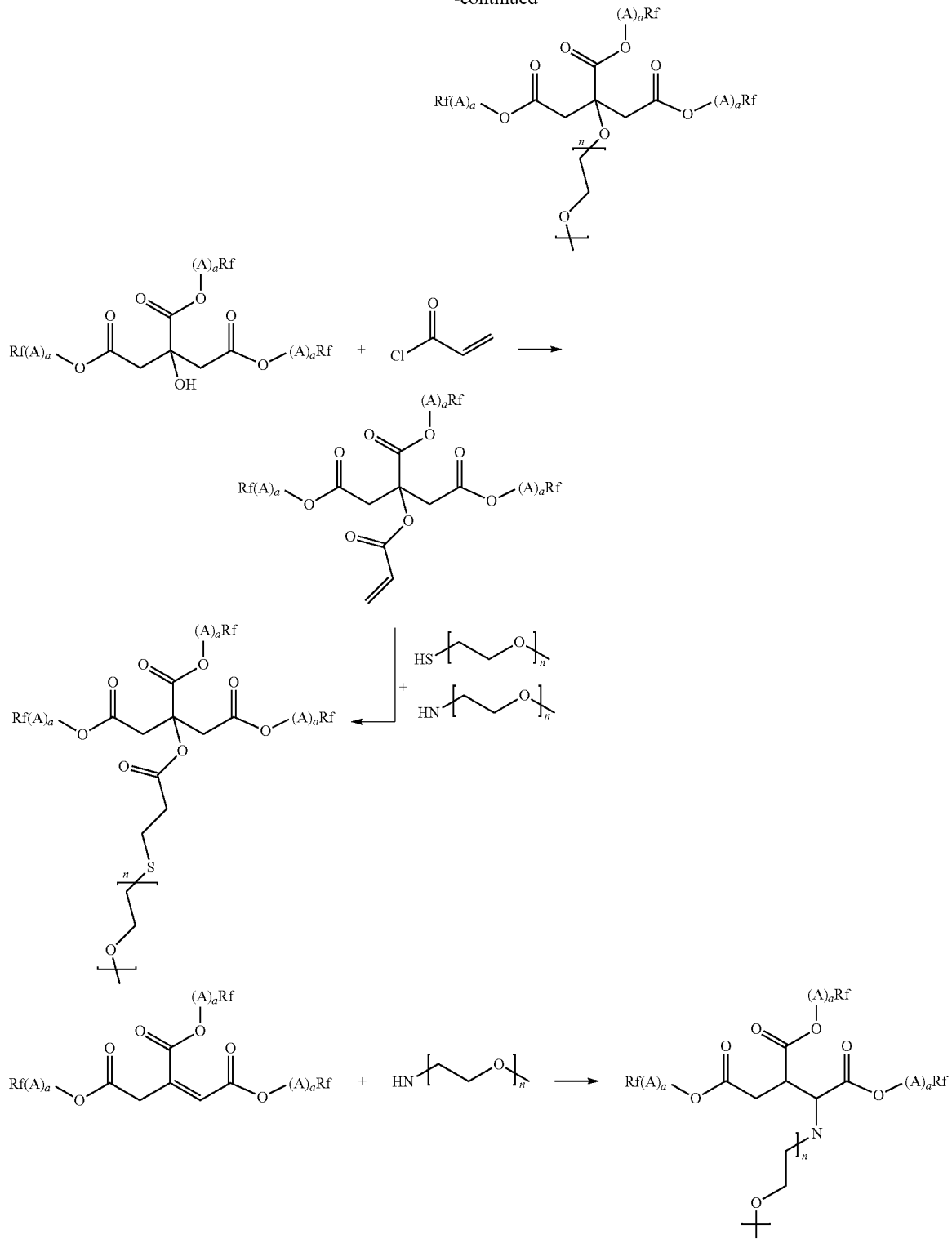

The preparation of further compounds of the formula (II) according to the invention can be carried out analogously to the illustrative reactions shown above. The preparation of further compounds of the formula (II) according to the invention can also be carried out by other methods known per se to the person skilled in the art from the literature. In particular, other esterification catalysts can be used.

These said syntheses are described in WO 2010/149262, WO 2011/082770 and WO 2012/084118. The disclosure contents in the cited references hereby expressly also belong to the disclosure content of the present application.

Compounds of the formula IV-1 or -2 can be obtained, for example, from the corresponding fluoroalcohols by reaction with fuming sulfuric acid. Compounds such as IV-3 or IV-4 are obtained, for example, by reaction of the corresponding fluoroolefin ether with hydrogensulfite.

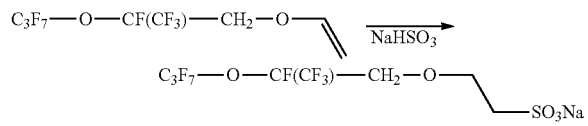

Compounds of the structure IV-5 to IV-8 can be obtained, for example, from the corresponding dimethylaminofluoro compounds by reaction with chloroacetic acid or by reaction with 1-chloro-2-hydroxyalkyl-ω-sulfonic acid.

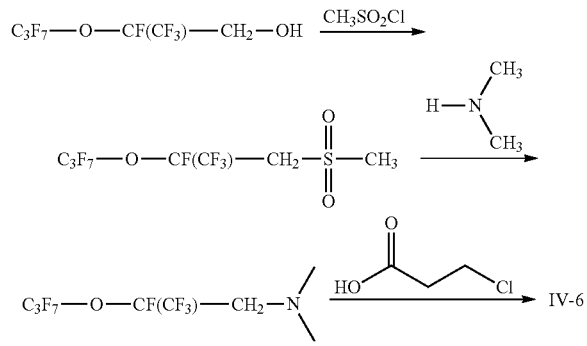

Compounds of the formula (III) where Rf=CF$_3$—CF$_2$—CF$_2$—O—CF(CF$_3$)—CO— can preferably be prepared by reaction of diaminoolefins with the corresponding fluorinated esters, acids or acid chlorides and addition onto the double bond in order to introduce the group X by methods known to the person skilled in the art.

Compounds of the formula (III) where Rf=Rf'=CF$_3$—CF$_2$—CF$_2$—O—CF(CF$_3$)—CH$_2$—O—CH$_2$—CHR'— can preferably be prepared by reaction of diaminoolefins with the corresponding fluorinated esters, acids or acid chlorides, addition onto the double bond in order to introduce the group X and reduction by methods known to the person skilled in the art.

Diaminoolefins are accessible, for example, from the corresponding halides via the Gabriel synthesis.

Symmetrical or asymmetrical dicarboxylic acid ester olefins, which can be converted into suitable starting materials by aminolysis and subsequent reduction, can be prepared by means of metathesis.

Compounds of the formula III-5 can be prepared, for example, by the following synthesis scheme:

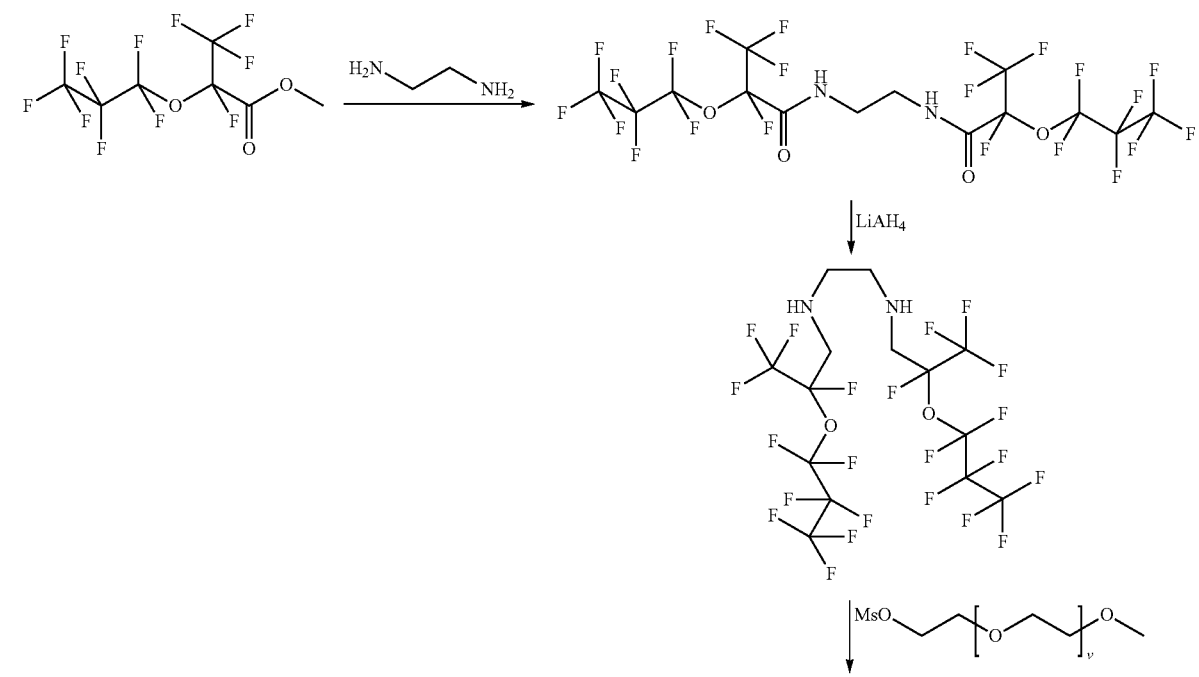

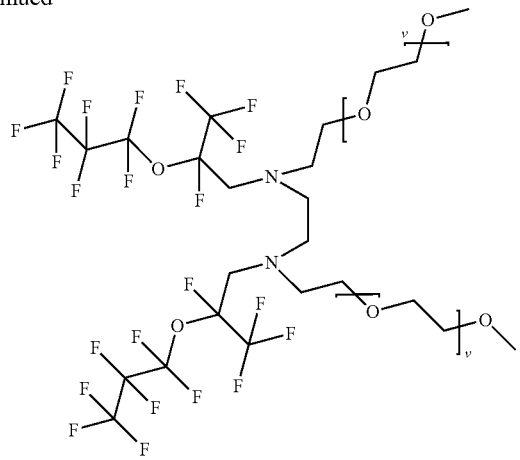

20

The preparation of further compounds according to the invention can be carried out analogously to the illustrative reactions shown above or by other methods known per se to the person skilled in the art from the literature.

Advantages of the compounds according to the invention may be, in particular:
- a surface activity which is equal or superior to that of conventional hydrocarbon surfactants with respect to efficiency and/or effectiveness,
- biological and/or abiotic degradability of the substances without formation of persistent perfluorinated degradation products, such as PFOA (perfluorooctanoic acid) or PFOS (perfluorooctanesulfonate),
- weak foaming action and/or low foam stabilisation,
- good processability in formulations and/or
- storage stability.

The compounds according to the invention preferably have a particular surface activity. The compounds of the formula (I) according to the invention, in particular the compounds of the formula (II), may have significantly improved environmental properties compared with the fluorosurfactants of the prior art since they do not degrade either chemically or biologically to form long-chain PFCAs or PFASs.

The present invention relates secondly to the use of the compounds according to the invention and the preferred embodiments described above as surface-active agents, for example for improving the flow behaviour and wetting capacity of coating formulations. Preference is given to the use of fluorosurfactants of the formulae (II), (Ill) and (IV), in particular the particularly preferred compounds mentioned.

Besides the compounds of the formula (I), the mixtures according to the invention may also comprise solvents, additives, assistants and fillers as well as non-fluorinated surfactants. Mention may be made by way of example of silicone particles, plasticisers and surface-modified pigments Preferred areas of use are, for example, the use of the fluorosurfactants according to the invention as additives in preparations for surface coating, such as paints, lacquers, protective coatings, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, floorcoverings and automobiles, in particular in floor polishes, in fire-extinguishing compositions, lubricants, or in photolithographic processes, in particular in immersion photolithography processes, for example in developer solutions, rinse solutions, immersion oils and/or in the photoresists themselves, especially for the production of printed circuits or in additive preparations for corresponding preparations.

In addition, the compounds which can be used in accordance with the invention as surfactant are suitable for washing and cleaning applications, and for use as additives/surfactants in cosmetic products, such as, for example, hair and bodycare products (for example shampoos, hair rinses and hair conditioners), foam baths, creams or lotions having one or more of the following functions: emulsifiers, wetting agents, foaming agents, lubricants, antistatic, enhancers of resistance to skin oils.

The fluorosurfactants according to the invention are, for use, usually introduced into correspondingly designed preparations. Usual use concentrations are 0.01-1.0% by weight of the surfactants according to the invention, based of the entire preparation. The present invention likewise relates to corresponding compositions comprising the fluorosurfactants according to the invention. Such compositions preferably comprise a vehicle which is suitable for the respective application, and optionally further active substances and/or optionally assistants. Preferred compositions are paint and coating preparations, fire-extinguishing agents, lubricants, washing agents and detergents and de-icers or developer solutions, rinse solutions, immersion oils and photoresists for photolithographic processes, in particular for immersion photolithography processes and in particular for the production of printed circuits, agrochemicals, floor polishes, cosmetic products, cosmetic products or hydrophobicisation agents for textile finishing or glass treatment. Preferred compositions here are paint and coating preparations and printing inks.

In addition, the present invention also relates to water-based surface-coating formulations which comprise the fluorosurfactants according to the invention, alone or mixed with additives. Preference is given to the use of surface-coating formulations based on the following synthetic film formers: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in surface coatings based on natural products and modified natural products. Preference is given to surface coatings based on oils, polysaccharides, such as starch and cellulose, and also based on natural resins, such as cyclic oligoterpenes, polyterpenes and/or shellac.

The fluorosurfactants according to the invention can be used both in physically hardening (thermoplastics) and in crosslinking (elastomers and thermosets) aqueous surface-coating systems. The fluorosurfactants according to the invention preferably improve the flow and wetting properties of the surface-coating systems.

The present invention relates to all uses mentioned here of fluorosurfactants to be employed in accordance with the invention. The respective use of fluorosurfactants for the said purposes is known to the person skilled in the art, and consequently the use of the fluorosurfactants to be employed in accordance with the invention presents no problems.

The complete disclosure contents of all applications and publications mentioned are incorporated into this application by way of reference. For the present invention, both the plural form of a term and also the singular form of a term also means the respective other form, unless expressly indicated otherwise. All features of the present invention can be combined with one another in any way, unless certain features are mutually exclusive. This applies, in particular, to preferred and particularly preferred features. Further features, advantages and variants of the invention also arise from the claims and examples. The following examples explain the present invention in greater detail without restricting the scope of protection.

EXAMPLES

Abbreviations
CaCl$_2$ calcium chloride
Et$_2$O diethyl ether
LiAlH$_4$ lithium aluminium hydride
EtOAc ethyl acetate or ethyl ethanoate
Na$_2$SO$_4$ sodium sulfate
H$_2$O water
MTBE tert-butyl methyl ether
NaCl sodium chloride Example 1

Synthesis of 1H,1H-perfluoro(2-methyl-3-oxa-hexan-1-ol) (CAS 2101-3-71)

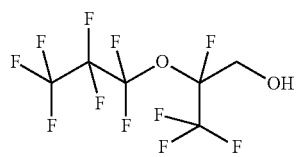

30 ml of abs. Et$_2$O are initially introduced in a dry 500 ml four-necked flask with metal condenser, CaCl$_2$ drying tube, dropping funnel and thermometer, and 70 ml of 1M LiAlH$_4$ solution (0.07 mol) in Et$_2$O are introduced via a septum. 44.30 g (0.12 mol) of methyl perfluoro(2-methyl-3-oxa-hexanoate) (ABCR, Karlsruhe Germany) in 50 ml of abs. Et$_2$O are introduced into the dropping funnel.

The ester is added dropwise with stirring at such a rate that the exothermicity of the reaction maintains the diethyl ether at the boil. When the addition is complete, the reaction mixture is stirred under reflux for a further 1.5 hours. A cloudy dispersion forms in the course of the reaction. The batch is cooled in an ice bath. The excess LiAlH$_4$ is decomposed by addition of 10 ml of EtOAc with slight evolution of heat. 10 g of H$_2$O are subsequently added, after which a flocculent aluminium hydroxide precipitate forms. 78 g of 25% sulfuric acid is added dropwise to the suspension over the course of 30 minutes, during which a clear two-phase mixture forms. The organic phase is separated off, and the aqueous phase is washed with 3×40 ml of Et$_2$O. The organic phases are combined, washed with 3×40 ml of H$_2$O and dried over Na$_2$SO$_4$. The ether is distilled off, and the residue is subjected to fractional distillation. Product: 31.8 g (b.p. 57° C./100 mbar); purity 91% (GC-MS); yield 73% of theory Example 2

Synthesis of 2-(2,3,3,3-tetrafluoro-2-heptafluoropropyloxy-propoxy)ethanol

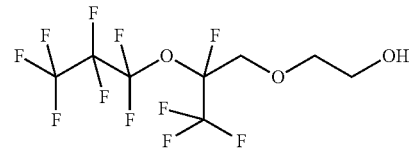 [SMILES: OCCOCC(F)(OC(F)(F)C(F)(F)C(F)(F)F)C(F)(F)F]

8.34 g (20 mmol) of 1H,1H-perfluoro(2-methyl-3-oxa-hexan-1-ol) are stirred under reflux for 48 hours together with 2.33 g (30 mmol) of ethylene carbonate and 0.33 g (2.4 mmol) of potassium carbonate. 25 ml of semi-concentrated hydrochloric acid and 25 ml of MTBE are added to the reaction mixture, and the phases are separated.

The aqueous phase is extracted with 2×25 ml of MTBE, and the combined org. phases are washed with 1×30 ml of water and 1×30 ml of saturated NaCl solution and dried over sodium sulfate. The solvent is removed in vacuo at 400 mbar and 40° C., and the residue is subjected to fractional distillation. Product: 6.5 g (b.p. 37° C./0.5 mbar); purity 85.3% (GC-MS); yield 64% of theory Example 3

Synthesis of Maleic Acid Esters with Chain-Extended Fluoroalcohols

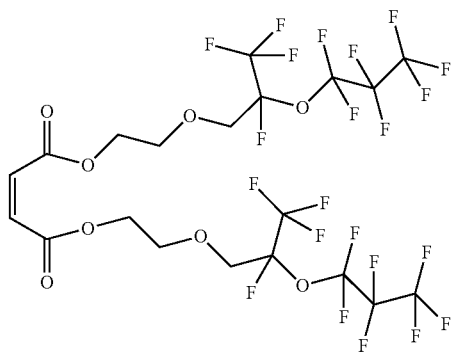 [SMILES: O=C(/C=C\C(=O)OCCOCC(F)(OC(F)(F)C(F)(F)C(F)(F)F)C(F)(F)F)OCCOCC(F)(OC(F)(F)C(F)(F)C(F)(F)F)C(F)(F)F]

21 mmol of chain-extended fluoroalcohol, 10 mmol of maleic anhydride and 2 mmol of p-toluenesulfonic acid in 0.47 mol of toluene are stirred under reflux. During the reaction, the water being liberated is removed with the aid of the water separator.

The reaction is followed by means of TLC control (reaction time 24-48 h). DI water is added, and the phases are separated.

The aqueous phase is subsequently extracted with 3×100 ml of MTBE, the combined organic phases are washed with 1×200 ml of water and 1×200 ml of saturated NaCl solution and dried over sodium sulfate and filtered. The solvent is distilled off in a rotary evaporator. The crude product is purified by fractional distillation. Yield for (Z)-but-2-enedioic acid bis[2-(2,3,3,3-tetrafluoro-2-heptafluoropropyloxypropoxy)ethyl]ester=98%

Example 4

Synthesis of Sulfosuccinates for the Example of Sodium 2-sulfosuccinate bis[2-(2,3,3,3-tetrafluoro-2-heptafluoropropyloxypropoxy)ethyl]ester

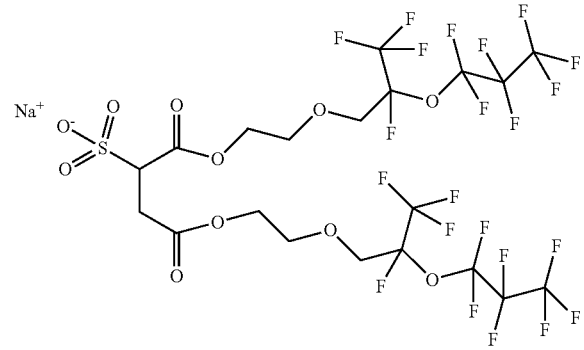 [SMILES: [Na+] ; O=C(CC(C(=O)OCCOCC(F)(OC(F)(F)C(F)(F)C(F)(F)F)C(F)(F)F)S(=O)(=O)[O-])OCCOCC(F)(OC(F)(F)C(F)(F)C(F)(F)F)C(F)(F)F]

Sodium hydrogensulfite solution (5 mole equivalents) is added dropwise at 50° C. to a solution of the maleic acid ester (1 mole equivalent) in 2-propanol (100 mole equivalents), and the mixture is subsequently stirred under reflux for a further 72 hours. 70 ml of water are added, and the mixture is extracted with 3×50 ml of MTBE. The combined organic phases are washed with 1×50 ml of water and saturated NaCl solution and dried over sodium sulfate. The solvent is removed in a rotary evaporator. Yield: 94%

Example 5

Determination of the Static Surface Tension

The static surface tensions γ of aqueous surfactant solutions having various concentrations c (grams per litre) are determined.
Instrument: Dataphysics tensiometer (model DCAT 11)
Temperature of the measurement solutions: 20°±0.2° C.
Measurement method employed: measurement of the surface tension using the Wilhelmy plate method in accordance with DIN EN 14370.
Plate: platinum, length=19.9 mm In the plate method, the surface or interfacial tension of the surfactant solution is calculated from the force acting on the wetted length of a plate, in accordance with the following formula:

$$\gamma = \frac{F}{L \cdot \cos\theta} = \frac{F}{L}$$

γ=interfacial or surface tension; F=force acting on the balance; L=wetted length (19.9 mm); δ=contact angle.

The plate consists of roughened platinum and is thus optimally wetted so that the contact angle δ is close to 0°. The term cos δ therefore approximately reaches the value 1, so that only the measured force and the length of the plate have to be taken into account.

The measurement values for the sulfosuccinate in accordance with Example 4 are reproduced in Table 1. FIG. 1 shows the static surface tension as a function of the concentration for the sulfosuccinate in accordance with Example 4.

TABLE 1

| c [g/l] | γ[mN/m] |
|---------|---------|
| 0.0003 | 57.8 |
| 0.0005 | 50.9 |
| 0.0008 | 44.8 |
| 0.00132 | 39.2 |
| 0.00216 | 35.2 |
| 0.00354 | 31.8 |
| 0.00579 | 28.6 |
| 0.00949 | 24.3 |
| 0.01554 | 20.6 |
| 0.02545 | 17.7 |
| 0.04169 | 16.8 |
| 0.06828 | 17.2 |
| 0.11183 | 18.8 |
| 0.18316 | 18.5 |
| 0.3 | 17.4 |
| 0.5 | 16.4 |
| 1 | 16.1 |

Example 6

Determination of the Dynamic Surface Tension

The dynamic surface tension γ of a 0.1% (per cent by weight) aqueous solution of the compound to be investigated is determined.
Measurement method employed: measurement of the surface tension using the bubble pressure method
Instrument: SITA tensiometer (model t 60)
Temperature of the measurement solutions: 20° C.±0.2° C.

In the measurement of the dynamic surface tension, air bubbles are forced through a capillary into the surfactant solution at different speeds. The surface tension can be determined from the resultant pressure change as a function of the bubble lifetime using the following equation:

$$\gamma = \frac{r(p_{max} - \rho \cdot g \cdot h)}{2}$$

$p_{max}$=maximum pressure, ρ=density of the liquid, h=immersion depth, r=radius of the capillary.

The measurement values for the sulfosuccinate in accordance with Example 4 are reproduced in Table 2. FIG. 2 shows the dynamic surface tension as a function of the bubble lifetime for the sulfosuccinate in accordance with Example 4.

TABLE 2

| Bubble lifetime [ms] | γ [mN/m] |
|----------------------|----------|
| 32 | 70.6 |
| 38 | 70.8 |
| 52 | 70.5 |
| 65 | 69.8 |
| 84 | 69.3 |

TABLE 2-continued

| Bubble lifetime [ms] | γ [mN/m] |
|---|---|
| 111 | 68.6 |
| 144 | 67.4 |
| 189 | 66 |
| 243 | 64 |
| 311 | 61.2 |
| 407 | 56.7 |
| 529 | 51.2 |
| 678 | 44.3 |
| 900 | 35 |
| 1033 | 29 |
| 1318 | 23.1 |
| 1798 | 19.4 |
| 2615 | 18.4 |
| 9738 | 15.9 |
| 12349 | 15.1 |
| 16176 | 14.9 |
| 19920 | 14.7 |
| 31841 | 14.4 |
| 33091 | 14.3 |
| 47713 | 14.2 |
| 60227 | 14.1 |

BRIEF DESCRIPTION OF FIGURES

FIG. 1: Static surface tension γ of the sulfosuccinate according to Example 4

FIG. 2: Dynamic surface tensions γ of the sulfosuccinate according to Example 4

The invention claimed is:

1. A compound of formula (I)

$$(R_f\text{-}A_a\text{-}C_c)_n\text{-}(spacer)_m\text{-}X_o \qquad (I)$$

wherein either a) or b) provides the definitions for the elements of formula (I)

a)
$Rf=CF_3—CF_2—CF_2—O—CF(CF_3)—CH_2—$,
$A=—O—CH_2—CHR'—$,
$R'=H$ or alkyl,
$C=$alkylene, $O$, $—OCO—$ or $—NR''—$,
$R''=H$, alkyl or $(CH_2CHR''')_{m'}—R''''$,
$m'=$an integer of 1 to 100,
$R'''$ and $R''''=$independently of one another, H or alkyl, in which one or more non-adjacent C atoms are optionally replaced by O or N,
spacer=a saturated or unsaturated, branched or unbranched hydrocarbon unit, optionally containing heteroatoms,
$X=$an anionic, cationic, non-ionic or amphoteric hydrophilic group,
non-ionic hydrophilic group=is $R^4—(O—CH_2CHR^5)_{m''}—$, $—CH(OH)—CH_2—NH\text{-Sach}$, or $—Y—(CH_2—CH_2—O)_v—R^{4'}$,
$m''=$an integer of 1 to 100,
$R^4$ and $R^5=$independently of one another H or $C_1$-$C_4$-alkyl,
Sach=a sugar,
$Y=S$, O or NH,
$R^{4'}=H$ or alkyl and
$v=1$-100,
$a=0$ or 1, and $a=1$, if $X=$an anionic hydrophilic group,
$n=2, 3, 4, 5$ or 6,
$c=0$ or 1,
$m=0$ or 1, and $o=1, 2, 3$ or 4, and $o=0$ if $R''=—(CH_2CHR''')_{m'}—R''''$, wherein $R'''$ and/or $R''''=$alkyl, wherein one or more non-adjacent C atoms have been replaced by O or N, or b)
$Rf=CF_3—CF_2—CF_2—O—CF(CF_3)—CO—$,
$A=—O—CH_2—CHR'—$,
$R'=H$ or alkyl,
$C=$alkylene, $O$, $—OCO—$ or $—NR''—$,
$R''=H$, alkyl or $(CH_2CHR''')_{m'}—R''''$,
$m'=$an integer of 1 to 100,
$R'''$ and $R''''=$independently of one another, H or alkyl, in which one or more non-adjacent C atoms are optionally replaced by O or N,
spacer=a saturated or unsaturated branched or unbranched hydrocarbon unit, optionally containing heteroatoms,
$X=$an anionic, cationic, non-ionic or amphoteric hydrophilic group,
non-ionic hydrophilic group=is $R^4—(O—CH_2CHR^5)_{m''}—$, $—CH(OH)—CH_2—NH\text{-Sach}$, or $—Y—(CH_2—CH_2—O)_v—R^{4'}$,
$m''=$an integer of 1 to 100,
$R^4$ and $R^5=$independently of one another H or $C_1$-$C_4$-alkyl,
Sach=a sugar,
$Y=S$, O or NH,
$R^{4'}=H$ or alkyl,
$v=1$-100,
$a=0$ or 1,
$n=2, 3, 4, 5$ or 6,
$c=0$ or 1,
$m=1$, and
$o=1, 2, 3$ or 4, and $o=0$ if $R''=—(CH_2CHR''')_{m'}—R''''$, wherein where $R'''$ and/or $R''''=$alkyl, wherein one or more non-adjacent C atoms have been replaced by O or N, and wherein
the following compounds are excluded:
$Rf'—O—CH_2CH(OSO_3Na)—CH_2—O—CH_2—CH—(C_2H_5)—C_4H_9$,
$Rf'—O—CH_2CH(OSO_3H)—(CH_2)_5—CH_3$,
$Rf'—O—CO—CH_2—CH(OSO_3Na)—CO—O—Rf'$,
$Rf''—CH_2—CH(SO_3Na)—Rf''$,
$Rf''—CH_2—CH(CH_2SO_3Na)—Rf''$ and
$Rf''—CH—(CH_3)CH(SO_3Na)—Rf''$,
wherein
$Rf'=CF_3CF_2CF_2—O—CF(CF_3)—CH_2—$, and
$Rf''=CF_3CF_2CF_2—O—CF(CF_3)—CO—NHCH_2CH_2—O—CO—$.

2. The compound of claim 1, wherein a) provides the definitions for the elements of formula (I), and wherein
$R'=H$ or $CH_3$,
$C=C_1$-$C_4$-alkylene, O or $—OCO—$,
spacer=aliphatic or aromatic hydrocarbon unit, optionally containing Heteroatoms,
$n=1, 2,$ or 3,
$c=1$, and
$o=1$ or 2.

3. A compound of claim 1, wherein a) provides the definitions for the elements of formula (I), and which is of formula (II)

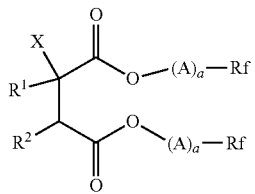

(II)

wherein
Rf=$CF_3$—$CF_2$—$CF_2$—O—$CF(CF_3)$—$CH_2$—,
A=—O—$CH_2$—CHR'—,
R'=H, $CH_3$, $C_2H_5$,
a=0 or 1,
X=an anionic, cationic non-ionic or amphoteric hydrophilic group,
non-ionic hydrophilic group=$R^4$—(O—$CH_2CHR^5$)$_{m''}$—, —CH(OH)—$CH_2$—NH-Sach, or —Y—($CH_2$—$CH_2$—O)$_v$—$R^{4'}$,
m''=an integer of 1 to 100,
$R^4$ and $R^5$=independently of one another H or $C_1$-$C_4$-alkyl,
Sach=a sugar,
Y=S, O or NH,
$R^{4'}$=H or alkyl,
v=1-100,
$R^1$=hydrogen or —$CH_2$—COO—(A)$_a$—Rf, and
$R^2$=hydrogen, —$CH_2$—COO—(A)$_a$—Rf or X.

4. The compound of claim 3, which is of formula (II-a):

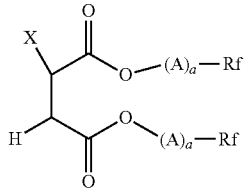

(II-a)

wherein
Rf=$CF_3$—$CF_2$—$CF_2$—O—$CF(CF_3)$—$CH_2$—,
A=—O—$CH_2$—CHR'—,
R'=H, $CH_3$, $C_2H_5$,
a=0 or 1, and
X=as defined for the compound of formula (II).

5. The compound of claim 3, which is of formula (II-b):

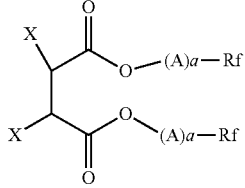

(II-b)

wherein
Rf=$CF_3$—$CF_2$—$CF_2$—O—$CF(CF_3)$—$CH_2$—,
A=—O—$CH_2$—CHR'—,
R'=H, $CH_3$, $C_2H_5$,
a=0 or 1, and
X=as defined for the compound of formula (II).

6. The compound of claim 3, which is of formula (II-c):

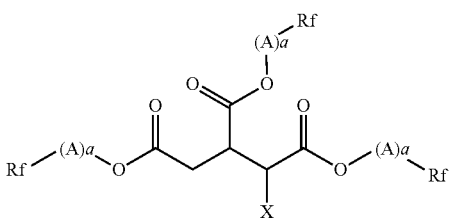

(II-c)

wherein
Rf=$CF_3$—$CF_2$—$CF_2$—O—$CF(CF_3)$—$CH_2$—,
A=—O—$CH_2$—CHR'—,
R'=H, $CH_3$, $C_2H_5$,
a=0 or 1, and
X=as defined for the compound of formula (II).

7. The compound of claim 3, which is of formula (II-d):

(II-d)

wherein a) provides the definitions for the elements of formula (I), and wherein
Rf=$CF_3$—$CF_2$—$CF_2$—O—$CF(CF_3)$—$CH_2$—,
A=—O—$CH_2$—CHR'—,
R'=H, $CH_3$, $C_2H_5$,
a=0 or 1, and
X=as defined for the compound of formula (II).

8. The compound of claim 1, wherein b) provides the definitions for the elements of formula (I), and wherein characterised
C=NR"—,
R"=H, alkyl or —($CH_2CHR'''$)$_{m'}$—R"",
m'=an integer of 1 to 100,
R'''=H or $C_1$-$C_4$-alkyl,
R""=alkyl, in which one or more non-adjacent C atoms have been replaced by O,
spacer=linear or branched alkylene,
X=as defined for the compound of formula (I),
a=0,
n=2 or 3,
c=1,
m=1, and
o=1 or 2, and o=0 if R"=—($CH_2CHR'''$)$_{m'}$—R"".

9. A compound of claim 1, wherein b) provides the definitions for the elements of formula (I), and which is of formula (III)

(III)

wherein
Rf=$CF_3$—$CF_2$—$CF_2$—O—$CF(CF_3)$—CO— or =Rf',
Rf'=$CF_3$—$CF_2$—$CF_2$—O—$CF(CF_3)$—$CH_2$—O—$CH_2$—CHR'—,
p=1-10,
q=1-10,
R'=H or alkyl,
R''=H, alkyl or $(CH_2CHR''')_{m'}$—R'''',
m'=an integer of 1 to 100,
R''' and R''''=independently of one another, H or alkyl, in which one or more non-adjacent C atoms are optionally replaced by O or N,
D and D'=H or X, wherein at least one group is equal to X if R''=H or alkyl,
X=an anionic, cationic, non-ionic or amphoteric hydrophilic group,
non-ionic hydrophilic group=$R^4$—$(O$—$CH_2CHR^5)_{m''}$—, —CH(OH)—$CH_2$—NH-Sach, or —Y—$(CH_2$—$CH_2$—O$)_v$—$R^{4'}$,
m''=an integer of 1 to 100,
$R^4$ and $R^5$=independently of one another H or $C_1$-$C_4$-alkyl,
Sach=a sugar,
Y=S, O or NH,
$R^{4'}$=H or alkyl,
v=1-100.

10. The compound of claim 9, wherein X is not —$SO_3^-$.

11. The compound of claim 9, wherein Rf=$CF_3$—$CF_2$—$CF_2$—O—$CF(CF_3)$—CO—, R''=H or alkyl and D and/or D'=X.

12. A compound of claim 1, wherein a) provides the definitions for the elements of formula (I), and which is of claim 1, formula (IV)

$$R_f\text{-}A_a\text{-}C\text{-}(spacer)mX \qquad (IV)$$

wherein
Rf=$CF_3$—$CF_2$—$CF_2$—O—$CF(CF_3)$—$CH_2$—,
A=—O—$CH_2$—CHR'—,
R'=H or alkyl,
C=alkylene or O,
X=an anionic, cationic non-ionic or amphoteric hydrophilic group,
non-ionic hydrophilic group=$R^4$—$(O$—$CH_2CHR^5)_{m''}$—, —CH(OH)—$CH_2$—NH-Sach, or —Y—$(CH_2$—$CH_2$—O$)_v$—$R^{4'}$,
m''=an integer of 1 to 100,
$R^4$ and $R^5$=independently of one another H or $C_1$-$C_4$-alkyl,
Sach=a sugar,
Y=S, O or NH,
$R^{4'}$=H or alkyl,
v=1-100,
a=0 or 1,
m=0 or 1.

13. The compound of claim 1, wherein a) or b) provides the definitions for the elements of formula (I), and wherein X is equal to —$SO_3^-$, —$OSO_3^-$, —$PO_3^{2-}$, —$OPO_3^{2-}$, —CH(OH)—$CH_2$—NH-Sach, wherein Sach=a sugar, or —Y—$(CH_2$—$CH_2$—O$)_v$R, wherein Y=S, O or NH and R=H or $CH_3$ and v=1-15.

14. The compound of claim 1, wherein a) or b) provides the definitions for the elements of formula (I), and wherein X is equal to —CH(OH)—$CH_2$—NH-Sach, wherein Sach=a sugar, or the group —Y—$(CH_2$—$CH_2$—O$)_v$R, wherein Y=S, O or NH and R=H or $CH_3$ and v=1-15.

15. The compound of claim 1, wherein a) provides the definitions for the elements of formula (I).

16. The compound of claim 1, wherein b) provides the definitions for the elements of formula (I).

17. The compound of claim 1, wherein b) provides the definitions for the elements of formula (I), and the spacer is a linear or branched alkylene.

18. The compound of claim 1, wherein b) provides the definitions for the elements of formula (I), and X is not —$SO_3^-$.

19. A compound of formula (I)

$$(R_f\text{-}A_a\text{-}C_c)_n\text{-}(spacer)_m\text{-}X_o \qquad (I)$$

wherein
Rf=$CF_3$—$CF_2$—$CF_2$—O—$CF(CF_3)$—$CH_2$—, $CF_3$—$CF_2$—$CF_2$— or $CF_3$—$CF_2$—$CF_2$—O—$CF(CF_3)$—CO—,
A=—O—$CH_2$—CHR'—,
R'=H or alkyl,
C=alkylene, O, —OCO— or —NR''—,
R''=H, alkyl or —$(CH_2CHR''')_{m'}$—R'''',
m'=an integer of 1 to 100,
R''' and R''''=independently of one another, H or alkyl, in which one or more non-adjacent C atoms are optionally replaced by O or N,
spacer=a saturated or unsaturated, branched or unbranched hydrocarbon unit, optionally containing heteroatoms,
X=—CH(OH)—$CH_2$—NH-Sach or —Y—$(CH_2$—$CH_2$—O$)_v$R,
Sach=a sugar,
Y=S, O or NH,
R=H or $CH_3$,
v=1-15,
a=0 or 1,
n=1, 2, 3, 4, 5 or 6,
c=0 or 1,
m=0 or 1, and
o=1, 2, 3 or 4, and o=0 if R''=—$(CH_2CHR''')_{m'}$—R'''', wherein where R''' and/or R''''=alkyl, wherein one or more non-adjacent C atoms have been replaced by O or N,
wherein n≥2 if Rf =$CF_3$—$CF_2$—$CF_2$—O—$CF(CF_3)$—CO—,
and wherein the following compounds are excluded
$CF_3$—$CF_2$—$CF_2$—O—$CH_2$—$CH_2$—OH,
Rf'—O—$CH_2CH(OSO_3Na)$—$CH_2$—O—$CH_2$—CH—$(C_2H_5)$—$C_4H_9$,
Rf'—O—$CH_2CH(OSO_3H)$—$(CH_2)_5$—$CH_3$,
Rf'—O—CO—$CH_2$—$CH(OSO_3Na)$—CO—O—Rf',
Rf''—$CH_2$—$CH(SO_3Na)$—Rf'',
Rf''—$CH_2$—$CH(CH_2SO_3Na)$—Rf'' and
Rf''—CH—$(CH_3)CH(SO_3Na)$—Rf'',
wherein
Rf'=$CF_3CF_2CF_2$—O—$CF(CF_3)$—$CH_2$—, and
Rf''=$CF_3CF_2CF_2$—O—$CF(CF_3)$—CO—$NHCH_2CH_2$—O—CO—.

20. A product selected from the group consisting of paints, coatings, printing inks, protective coatings, special coatings in electronic and optical applications, photoresists, top antireflective coatings and bottom antireflective coatings, developer solutions and washing solutions and photoresists for photolithographic processes, cosmetic products, agrochemicals, floor polishes, photographic coatings and coatings of optical elements, comprising a compound according to claim 1.

21. A composition comprising a compound according to claim 1, wherein the composition is selected from the group consisting of paint and coating preparations, fire-extinguishing compositions, lubricants, washing compositions and detergents, de-icers, developer solutions and washing solutions and photoresists for photolithographic processes, cosmetic products, agrochemicals, floor polishes and hydrophobicising compositions for textile finishing and glass treatment.

* * * * *